(12) United States Patent
Hayek et al.

(10) Patent No.: US 6,946,488 B2
(45) Date of Patent: Sep. 20, 2005

(54) PET FOOD COMPOSITION FOR REDUCING INFLAMMATORY RESPONSE IN CATS

(75) Inventors: Michael G. Hayek, Dayton, OH (US); Gregory Allen Reinhart, Dayton, OH (US)

(73) Assignee: The Iams Company, Dayton, OH (US)

( * ) Notice: Subject to any disclaimer, the term of this patent is extended or adjusted under 35 U.S.C. 154(b) by 0 days.

(21) Appl. No.: 09/845,941

(22) Filed: Apr. 30, 2001

(65) Prior Publication Data

US 2001/0051206 A1 Dec. 13, 2001

Related U.S. Application Data

(60) Provisional application No. 60/201,029, filed on May 1, 2000.

(51) Int. Cl.$^7$ .............................................. A61K 31/20
(52) U.S. Cl. ...................... 514/558; 514/560; 424/442
(58) Field of Search ................................ 514/558, 560; 424/442

(56) References Cited

U.S. PATENT DOCUMENTS

| | | | |
|---|---|---|---|
| 4,229,485 A | * | 10/1980 | Brown et al. |
| 5,656,312 A | | 8/1997 | Erasmus et al. |
| 5,756,088 A | | 5/1998 | Matsuura et al. |
| 5,834,048 A | | 11/1998 | Erasmus et al. |
| 6,001,401 A | | 12/1999 | Erasmus et al. |
| 6,042,857 A | | 3/2000 | Jones et al. |
| 6,071,544 A | | 6/2000 | Sunvold |

FOREIGN PATENT DOCUMENTS

| | | | |
|---|---|---|---|
| EP | 0678247 A1 | * | 10/1995 |
| EP | 0 678 247 | | 10/1995 |
| WO | WO 97/19683 | * | 6/1997 |
| WO | WO 0137678 A | | 5/2001 |

OTHER PUBLICATIONS

UC Berkeley Wellness Letter, Just the flax please, Jun. 1999, pp. 1–2.*

McLean, J.G., Monger, E.A.; "Factors determining the essential fatty acid requirements of the cat" Nutrition of the dog and cat. Waltham Symposium 7, 1989, pp. 329–342.

Frankel, T.L., Rivers, J.P.W.; "Fatty acid composition of tissues from omega 3–deficient and normal kittens" Proceedings of the Nutrition Society of Australia, vol. 13, 1988, pp. 141.

Van Niel, M.H., Beynen, A.C.; "The intake of polyunsaturated fatty acids by cats is reflected in their adipose tissue" Veterinary Quarterly, vol. 19, No. 4, Nov. 1997, pp. 150–153.

Hall, J.A. et al.; "Lipid composition of hepatic and adipose tissues from normal cats and from cats with idiopathic hepatic lipdosis" Journal of Veterinary Internal Medicine, vol. 11, No. 4, Jul.–Aug. 1997, pp. 238–242.

Pawlosky, R. et al.; "Essential fatty acid metabolism in the feline; relationship between liver and brain production of long–chain polyunsaturated fatty acids" Journal of Lipid Research, vol. 35, No. 11, Nov. 1994, pp. 2032–2040.

Boon P. Chew et al: "Anti–inflammatory action of dietary fish and flaxseed oils in cats", FASEB Journal, vol. 15, No. 4, 2001, p. A294.

R. Lechowski et al: "The effect of the additional of oil preparation with increased conttent of N–3 fatty acids on serum lipid profile and clinical condition of cats with miliary dermatitis", Journal of Veterinary Medicine, Series A, vol. 45, No. 6/7, 1998, pp. 417–424.

Michael G. Hayek et al: "Utilization of omega 3 fatty acids in companion animal nutrition" World Review of Nutrition and Dietetics, vol. 83, pp. 176–185.

* cited by examiner

*Primary Examiner*—Sreeni Padmanabhan
*Assistant Examiner*—Jennifer Kim
(74) *Attorney, Agent, or Firm*—Cynthia L. Clay; Kelly McDow-Dunham; Karen F. Clark

(57) ABSTRACT

A pet food composition and method is provided for reducing inflammatory response in cats. The method includes administering a pet food composition including omega-6 and omega-3 fatty acids in a weight ratio of about 5:1, where the majority of omega-3 fatty acids comprise alpha-linolenic acid. Flaxseed oil is the preferred source of alpha-linolenic acid.

6 Claims, 5 Drawing Sheets

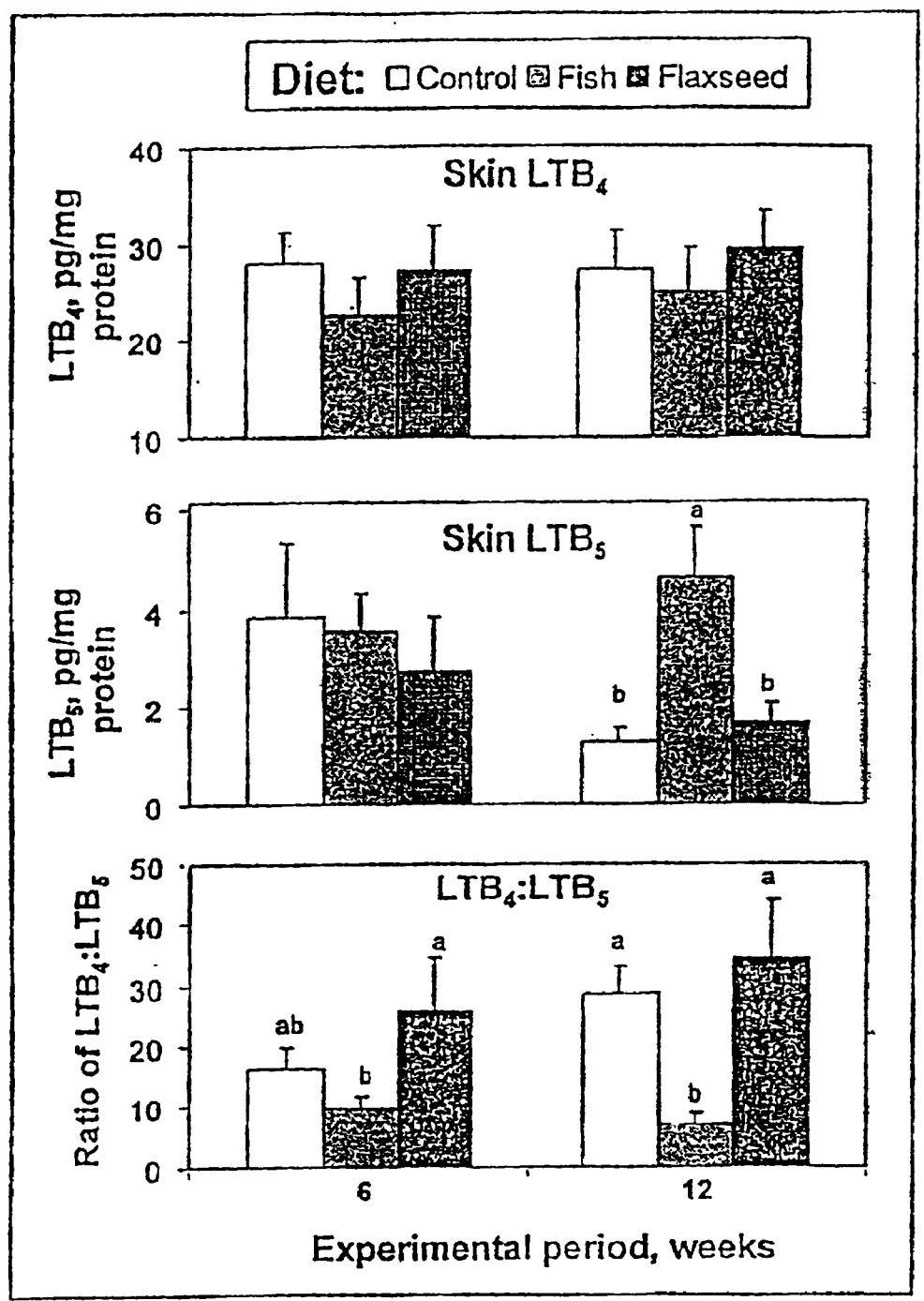
Figure 1. Skin leukotriene concentrations in cats fed control, fish oil, or flaxseed oil for 12 weeks (Experiment 1). Different letters associated with the means are significantly different, $P<.05$.

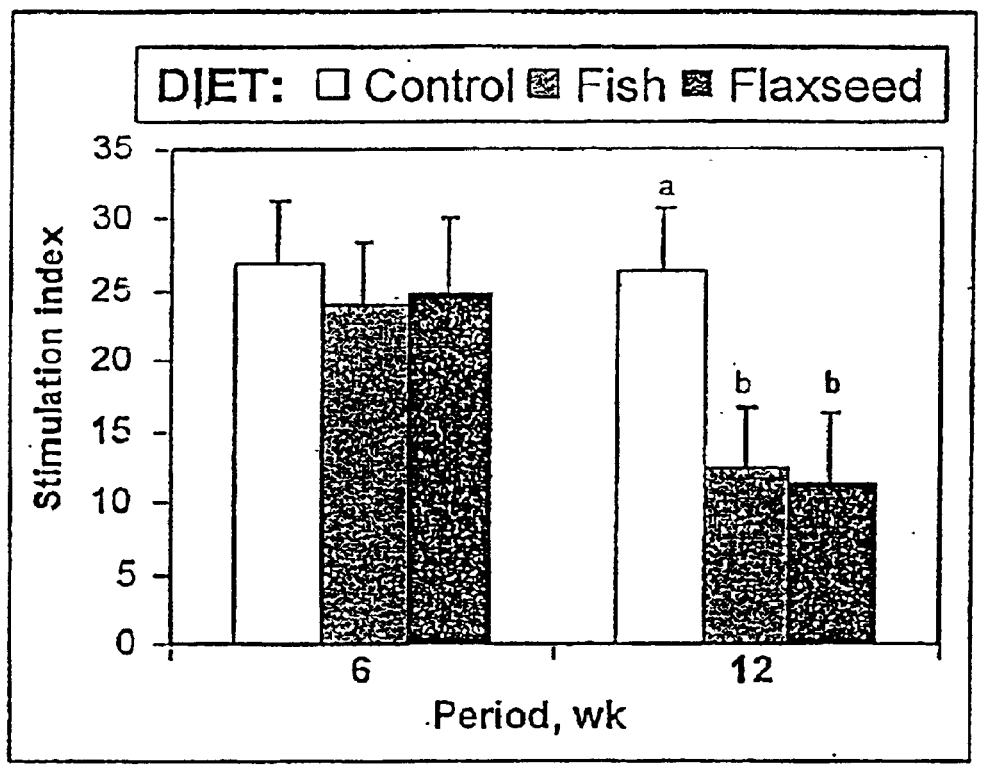
Figure 2. Stimulation of peripheral blood mononuclear cells proliferation by pokeweed mitogen in cats fed control, fish oil, or flaxseed oil (Experiment 1). Different letters associated with the means are significantly different, $P<.05$.

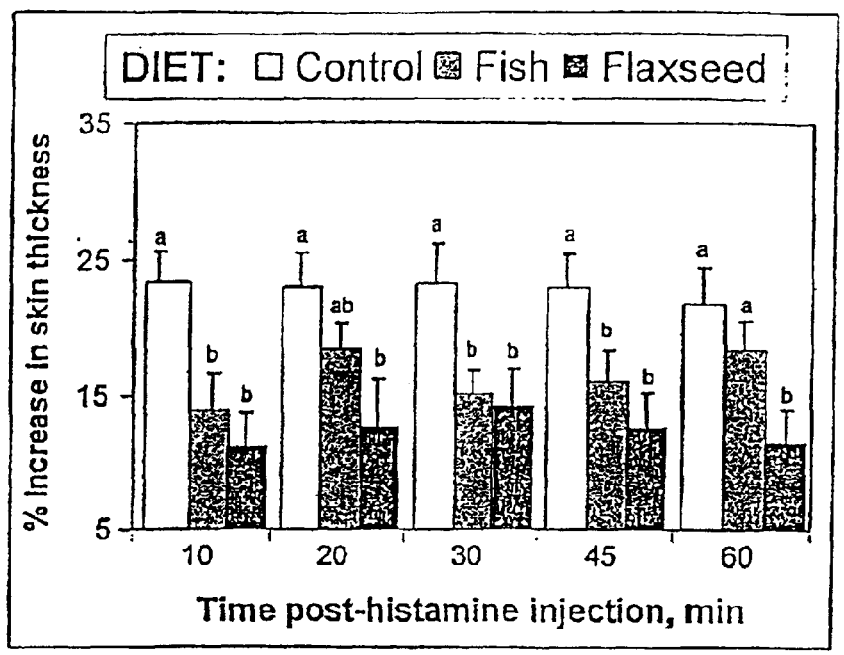

Figure 3 Skin hypersensitivity response to histamine in cats fed control, fish oil, or flaxseed oil (Experiment 2). Different letters associated with the means are significantly different, $P<.01$.

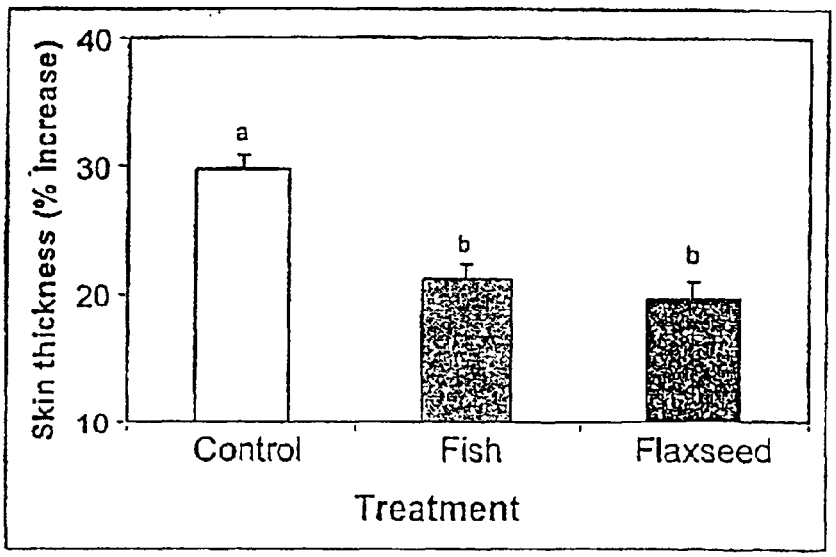

Figure 4 Maximal hypersensitivity type I response to histamine in cats fed control, fish oil, or flaxseed oil for 12 weeks (Experiment 2). Different letters associated with the means are significantly different, $P<.01$.

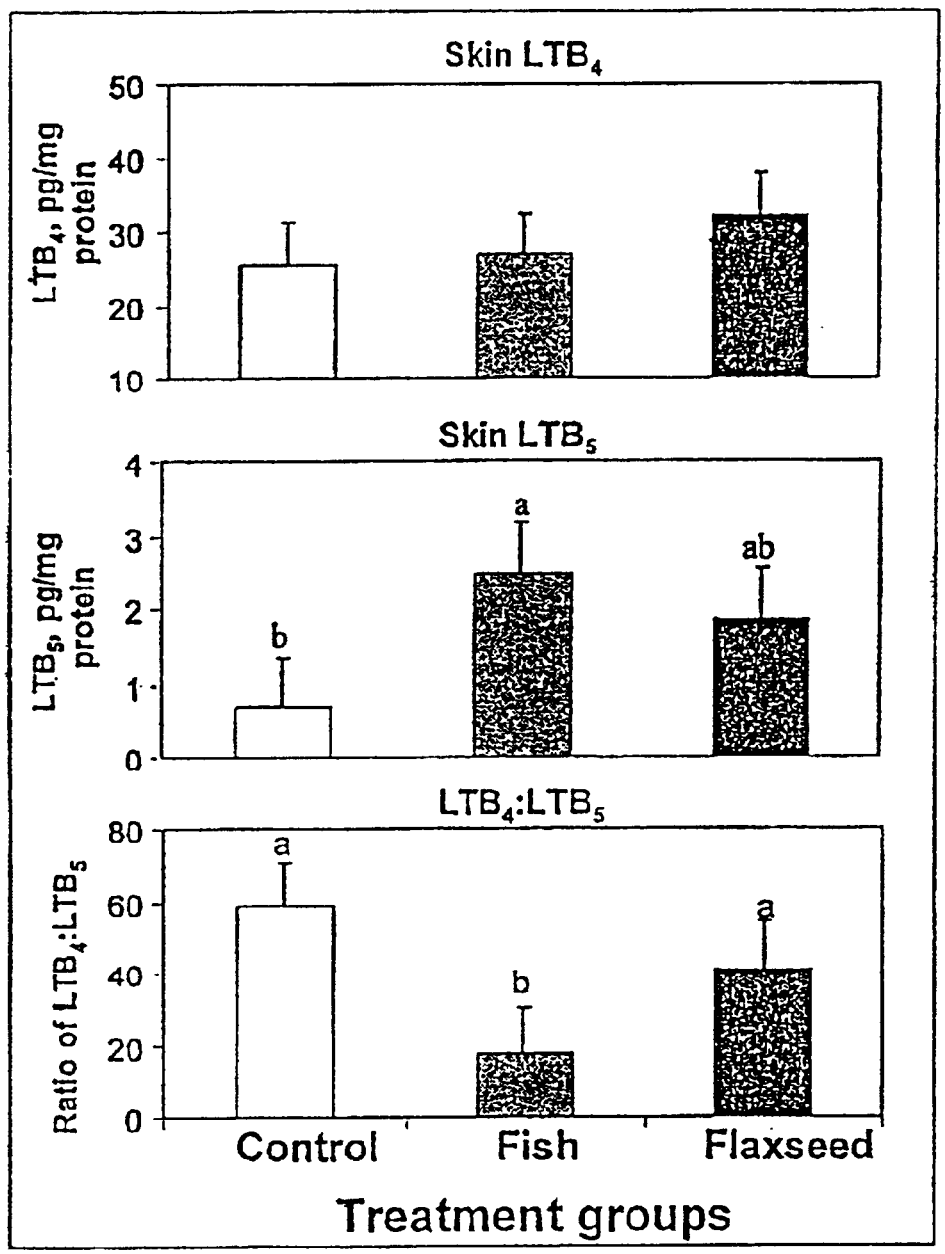
Figure 5 Skin leukotriene concentrations in cats fed control, fish oil, or flaxseed oil for 12 weeks. Different letters associated with the means are significantly different, $P<.05$.

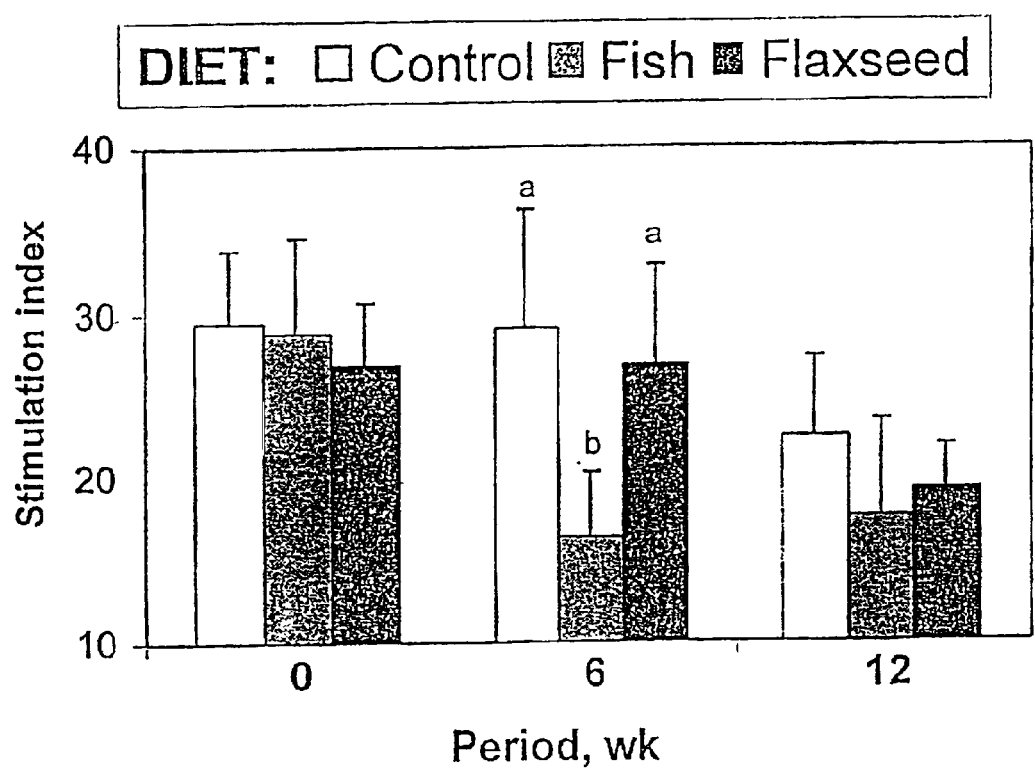
Figure 6 Stimulation of peripheral blood mononuclear cells proliferation by pokeweed mitogen in cats fed control, fish oil or flaxseed oil (Experiment 2). Different letters associated with the means are significantly different, $P<.05$.

PET FOOD COMPOSITION FOR REDUCING INFLAMMATORY RESPONSE IN CATS

CROSS REFERENCE TO RELATED APPLICATIONS

This application claims the benefit of U.S. provisional application Ser. No. 60/201,029, filed May 1, 2000.

FIELD OF THE INVENTION

This invention relates to a pet food composition and method for reducing inflammatory response in cats. More particularly, the invention relates to a feline dietary composition that includes omega-3 (n-3) fatty acids, especially the form of the omega-3 fatty acid known as alpha-linolenic acid, which, when provided to a cat, produces a reduction in the feline inflammatory response.

BACKGROUND OF THE INVENTION

Inflammation occurs when tissues are damaged. Inflammation can often be characterized by redness, swelling, heat, and pain. Cells involved in the inflammatory response include polymorphonuclear luekocytes (PMN), macrophages, and mast cells. One type of inflammatory response is an allergic response, or Type I hypersensitivity response. Upon exposure to an allergen, B cells produce immunoglobulin E (IgE), which complexes with mast cells, resulting in the release of toxic cytokines and inflammatory mediators such as histamine, protease, prostaglandin, and leukotriene. In atopic individuals, this IgE-mast cell complex persists longer, resulting in an over-production of mediators and in inflammation, with the key mediator of inflammation being histamine.

In felines, as in other animals, inappropriate or excess inflammatory response can cause significant health problems. For example, a number of disorders present on a regular basis for veterinary treatment, including inflammatory bowel disease, arthritis, and dermatitis. Some conditions may be treated with medication, but such medications may be expensive and they can often be accompanied by undesirable side effects. It would be preferable to provide relief from such conditions by means of components in the feline diet.

Lipids are recognized as important constituents of mammalian diets, and certain lipids have been demonstrated to have a direct impact on specific metabolic processes. One such group of lipids are the polyunsaturated fatty acids (PUFA's), which can generally be classified as omega-3 (n-3) or omega-6 (n-6) fatty acids. The essential fatty acid arachidonic acid, for example, is required for steroid synthesis and is recognized as having a role in both the immune response and the in cardiovascular disease. Both the n-6 and n-3 series of fatty acids have been shown to influence the inflammatory response through the eicosanoid pathway. Eicosanoids are metabolites of arachidonic acid or eicosapentaenoic acid which are released from cellular membranes in response to cell injury. Arachidonic acid is used in the production of certain prostaglandins, leukotrienes and thromboxanes that promote an inflammatory response. Eicosapentaenoic acid (EPA) is used in the production of certain prostaglandins, leukotrienes and thromboxanes that have been demonstrated to reduce the inflammatory response.

The ability of diet to influence eicosanoid production, thereby influencing the production of mediators of the inflammatory response, has been demonstrated in the dog. Studies have shown that altering the dietary omega-6 to omega-3 fatty acid ratio from 100:1 to 5:1 decreases skin production of LTB4 and increases skin production of LTB5, thus decreasing the inflammatory potential in those dogs.

In the dog, certain fatty acids can be derived from shorter chain fatty acids present in the diet. Dietary linoleic acid, for example, can be absorbed and elongated to form arachidonic acid with the help of specific canine elongase and desaturase enzymes. Alpha-linolenic acid (ALNA) can be elongated to form EPA using similar enzymes. In humans, ALNA can be desaturated and elongated to EPA and DHA. Cats, however, cannot utilize dietary C 18 essential fatty acids such as ALNA due to a lack of the necessary enzyme. It has been generally accepted, therefore, that cats require 20-carbon long chain essential fatty acids such as arachidonic acid. Feline requirements for essential fatty acids in the diet cats have generally not been determined, and little is known about the effects of dietary n-3 fatty acids on the feline immune system.

Accordingly, there is still a need in the art for a dietary composition for felines which provides sufficient levels of essential fatty acids to reduce inflammatory response.

SUMMARY OF THE INVENTION

The present invention meets that need by providing a pet food composition for cats including omega-3 fatty acids, preferably in the form of alpha-linolenic acid, to reduce inflammatory response.

In one aspect of the present invention, a pet food composition for reducing inflammatory response in cats is provided which comprises, on a dry matter basis, from about 7 to about 14% by weight fat, and omega-6 and omega-3 fatty acids in a weight ratio of about 5:1, where the majority of omega-3 fatty acids by weight comprise alpha-linolenic acid. Preferably, the source of alpha-linolenic acid in the composition is flaxseed oil.

Preferably, at least 20 wt % of the total fatty acids are omega-6 fatty acids and at least 4 wt % of the total fatty acids are omega-3 fatty acids.

The omega-3 fatty acids in the composition preferably further comprise eicosapentaenoic acid, docosahexaenoic acid, or a combination of the two.

The present invention also provides a method for reducing the feline inflammatory response by providing the composition of the present invention to cats in a quantity and frequency appropriate for their nutritional needs.

Accordingly, it is a feature of the present invention to provide a pet food composition and method for reducing inflammatory response in cats. This, and other features and advantages of the present invention, will become apparent from the following detailed description, the accompanying drawings, and the appended claims.

BRIEF DESCRIPTION OF THE DRAWINGS

FIG. 1 is a series of bar graphs showing the skin leukotriene concentrations in cats fed different diets for 12 weeks (Example 1);

FIG. 2 is a bar graph showing the stimulation of peripheral blood mononuclear cells in cats fed different diets (Example 1);

FIG. 3 is a bar graph showing the skin hypersensitivity response to histamine in cats fed different diets (Example 2);

FIG. 4 is a bar graph showing maximal hypersensitivity type I response to histamine in cats fed different diets (Example 2);

FIG. 5 is a bar graph showing skin leukotriene concentrations in cats fed different diets for 12 weeks (Example 2); and FIG. 6 is a bar graph showing stimulation of peripheral blood mononuclear cells in cats fed different diets (Example 2).

DETAILED DESCRIPTION OF THE PREFERRED EMBODIMENT

We have discovered that feeding cats a diet including alpha-linolenic acid as the primary source of omega-3 fatty acids produces a decreased inflammatory response. While one skilled in the art of feline nutrition would generally accept that an 18-carbon fatty acid such as alpha-linolenic acid would have no effect on eicosanoic and arachadonic acid synthesis, administration of alpha-linolenic acid provides a benefit to the cat by producing a reduction in the inflammatory response normally mediated by both eicosapentaenoic acid and arachidonic acid.

The pet food composition of the present invention preferably contains, on a dry matter basis, from about 7 to about 14% by weight total fat, including omega-6 and omega-3 fatty acids which are provided in a weight ratio of about 5:1. The majority of omega-3 fatty acids comprise alpha-linolenic acid. Preferably, the alpha-linolenic acid comprises at least 80% by weight of the total omega-3 fatty acids, and more preferably, at least 90% by weight. The source of alpha-linolenic acid is preferably a plant-based source such as flaxseed oil.

The dietary composition may be provided in any suitable form, provided that it contains the preferred concentrations and sources of fatty acids described herein. The composition may also be fortified with vitamins and micronutrients so that the diet consumed also provides for the other general nutritional needs of the cat. Suitable dietary compositions include, for example, dry kibble, moist chunk foods, moist canned cat food, or cat treats. When formulated according to the ratios described herein, the product can be provided to a cat according to regular feeding guidelines. Alternately, the product may be provided in more limited quantities or in additional quantities as desired by a veterinary professional, using feeding calculations known to those of skill in the art.

In order that the invention may be more readily understood, reference is made to the following example which is intended to illustrate the invention, but not limit the scope thereof.

EXAMPLE 1

To determine the potential beneficial effects of dietary n-3 PUFA from fish oil (marine source) and flaxseed oil (plant source) on immunity and inflammatory response in the domestic cat, cats were fed a high-lipid diet (22 wt % dietary lipids). Female tabby cats (19 to 20 months old, with an average body weight of 4.9 kg) were adapted to a nutritionally balanced diet (The Iams Co., Dayton, Ohio) for 12 weeks prior to assignment to groups of 14 cats per group in three groups: 1) cats fed the control diet, 2) cats fed a diet containing fish oil, or 3) cats fed a diet containing flaxseed oil. The experimental feeding protocol lasted for 12 weeks. All diets contained 22 wt % total lipids (Table 1). The control diet contained poultry fat, which is high in n-6 PUFA (n-6:n-3 PUFA ratio of about 20:1). Fish oil or flaxseed oil were mixed with the poultry fat in the other 2 diets to achieve the desired n-6:n:3 PUFA ratio of about 5:1. All other dietary ingredients remained constant across treatments.

TABLE 1

Dietary lipid composition in Experiment 1: 22% total lipid diet

| | Control | Fish oil | Flaxseed oil |
|---|---|---|---|
| Lipid (%) | 22.0 | 22.0 | 22.0 |
| Percent of total fatty acids | | | |
| Palmitic acid (16:0) | 23.0 | 22.6 | 22.3 |
| Linoleic acid (18:2n − 6) | 18.8 | 17.6 | 18.9 |
| γ-linolenic acid (18:3n − 6) | 0.2 | 0.2 | 0.2 |
| Arachidonic acid (20:4n − 6) | 0.8 | 0.8 | 0.7 |
| α-Linolenic acid (18:3n − 3) | 0.8 | 0.8 | 4.0 |
| Eicosapentaenoic acid (20:5n − 3) | 0.03 | 1.58 | 0.10 |
| Docosahexaenoic acid (22:6n − 3) | 0.09 | 0.67 | 0.13 |
| Total n − 6 PUFA | 20.3 | 19.2 | 20.4 |
| Total n − 3 PUFA | 1.1 | 3.7 | 4.5 |
| n − 6:n − 3 ratio | 20:1 | 5:1 | 5:1 |
| Vitamin E (mg/kg) | 110 | 110 | 110 |

Results

General. Diet composition in this study was not found to significantly affect body weight (average 4.9±0.1 kg) or food intake (average 76±4 g/d).

Fatty acid profile. Plasma total n-6 PUFA was higher in cats fed the control and flaxseed oil diets compared to those fed fish oil (Table 3). Cats fed flaxseed oil had plasma α-linolenic acid about 5-fold higher than those fed the control and fish oil diets. As expected, total n-3 PUFA was higher in cats fed the fish oil diet and the flaxseed oil diet than those fed the control diet. More specifically, cats fed fish oil had the highest concentration of plasma eicosapentaenoic acid (EPA) and docosahexaenoic acid (DHA). Consequently, the n-6:n-3 PUFA ratio was highest in cats fed the control diet and lowest in cats fed the diet containing fish oil. While the n-6:n-3 PUFA ratio was similar (5:1) in the plasma and the diet of cats fed fish oil, those fed the flaxseed oil had a higher n-6:n-3 PUFA ratio (Table 3) in the plasma (16:1) compared to the dietary source. This is due to 3-fold lower n-3 plasma levels compared to the cats fed the diet containing fish oil.

TABLE 2

Fatty acid composition (%) in plasma (Experiment 1)

| | | Diet | | |
|---|---|---|---|---|
| Fatty acid | Week | Control | Fish | Flaxseed |
| ALNA | 6 | 0.30[b] | 0.30[b] | 1.62[a] |
| (α-Linolenic acid) | 12 | 0.31[b] | 0.28[b] | 1.50[a] |
| EPA | 6 | 0.12[b] | 4.95[a] | 0.11[b] |
| (Eicosapentaenoic acid) | 12 | 0.11[b] | 4.96[a] | 0.12[b] |
| DHA | 6 | 0.77[b] | 1.68[a] | 0.55[c] |
| (Docosahexaenoic acid) | 12 | 0.64[b] | 1.74[a] | 0.59[b] |
| n − 6 PUFA | 6 | 38.7[a] | 33.9[b] | 37.8[a] |
| | 12 | 39.2[a] | 34.3[b] | 39.2[a] |
| n − 3 PUFA | 6 | 1.42[c] | 7.67[a] | 2.47[b] |
| | 12 | 1.25[c] | 7.71[a] | 2.40[b] |
| n − 6:n − 3 | 6 | 27.93[a] | 4.45[c] | 15.44[b] |
| | 12 | 31.49[a] | 4.51[c] | 16.46[b] |

Different subscripts among diets but within a period indicate a significant statistical difference, P < .05. (PUFA - polyunsaturated fatty acids)

The fatty acid profile in the skin (Table 3) mirrored that found in plasma (Table 2). Overall, total n-6 PUFA in the skin was the highest in cats fed the control diet, whereas total n-3 PUFA was higher in cats fed the fish oil and flaxseed oil diets. The ratio of n-6:n-3 was significantly lower in cats fed the fish and flaxseed oil diets than in control. Cats fed fish and flaxseed oils had a skin n-6:n-3 PUFA ratio of 11:1, which was lower than the control. There was no difference in total n-3 fatty acids, although cats fed fish oil had higher EPA and DHA while cats fed flaxseed oil had higher ALNA.

TABLE 3

Fatty acid composition (%) in the skin (Experiment 1)

| Fatty acid | Week | Control | Fish | Flaxseed |
|---|---|---|---|---|
| ALNA | 6 | 0.67[b] | 0.68[b] | 1.21[a] |
| (α-Linolenic acid) | 12 | 0.62[b] | 0.63[b] | 1.25[a] |
| EPA | 6 | 0.04[b] | 0.26[a] | 0.05[b] |
| (Eicosapentaenoic acid) | 12 | 0.04[b] | 0.23[a] | 0.04[b] |
| DHA | 6 | 0.23[b] | 0.37[a] | 0.23[b] |
| (Docosahexaenoic acid) | 12 | 0.21[b] | 0.33[a] | 0.20[b] |
| n-6 PUFA | 6 | 17.42[a] | 16.95[b] | 17.11[a] |
|  | 12 | 17.26 | 16.92 | 17.06 |
| n-3 PUFA | 6 | 1.11[b] | 1.59[a] | 1.65[a] |
|  | 12 | 1.02[b] | 1.48[a] | 1.63[a] |
| n-6:n-3 | 6 | 15.85[a] | 10.87[b] | 10.57[b] |
|  | 12 | 17.19[a] | 11.67[b] | 10.86[b] |

Different subscripts among diets but within a period indicate a significant statistical difference, P < .05. (PUFA-polyunsaturated fatty acids)

The possible conversion of ALNA to longer chain fatty acids was analyzed by comparing the proportion of ALNA, EPA, and DHA in plasma and skin. The EPA and DHA content of plasma and skin in cats fed the control and the flaxseed oil diets were generally similar, even though the ALNA content of cats fed the flaxseed oil was higher, indicating insignificant conversion of ALNA to the longer chain n-3 PUFA in felines.

Skin Leukotrine production. Diet did not significantly affect concentration of skin $LTB_4$. However, cats fed the diet containing fish oil had significantly higher concentration of $LTB_5$ in the skin at week 12 (FIG. 1). Consequently, the ratio of $LTB_4$:$LTB_5$ was lowest in cats fed the diet containing fish oil. Dietary flaxseed oil did not significantly influence the concentration of $LTB_4$ or $LTB_5$ in the skin.

Lymphocyte Proliferation. Cats fed fish oil and flaxseed oil had lower PBMC proliferation in response to PWM compared to control after 12 weeks of feeding (FIG. 2). No significant dietary effect was observed with the T cell mitogens, Con A and PHA.

Leukocyte Subpopulations. The population of CD21+ B cells also was lower on week 12 in cats fed fish oil and flaxseed oil compared to those fed the control diet (Table 4). Lower B cell subpopulations may help explain the lower proliferative response to PWM observed in cats fed the same diets. No dietary treatment effects were observed with the populations of $CD5^+$ total T cells, $CD4^+$ Tc cells, $CD8^+$ Tc cells, and MHC $II^+$ activated macrophages.

TABLE 4

Percentages of blood leukocyte subpopulations in cats fed control, fish oil or flaxseed oil diet for 12 weeks (Experiment 1)

|  | Period, Week | Control | Fish | Flaxseed |
|---|---|---|---|---|
| $CD5^+$ T cells | 6 | 69.4 ± 1.2 | 67.6 ± 2.4 | 67.9 ± 2.9 |
|  | 12 | 63.4 ± 3.9 | 63.0 ± 4.0 | 58.9 ± 3.9 |
| $CD4^+$ T cells | 6 | 31.7 ± 1.5 | 32.2 ± 2.0 | 28.5 ± 2.2 |
|  | 12 | 23.2 ± 4.1 | 22.1 ± 4.0 | 20.8 ± 3.3 |
| $CD8^+$ T cells | 6 | 16.9 ± 2.2 | 13.1 ± 1.7 | 18.1 ± 3.3 |
|  | 12 | 6.4 ± 0.9 | 10.9 ± 1.5 | 9.7 ± 1.8 |
| MHC $II^+$ | 6 | 52.5 ± 4.9 | 52.8 ± 5.3 | 54.9 ± 4.8 |
| cells | 12 | 54.4 ± 5.3 | 55.1 ± 4.7 | 51.8 ± 4.7 |
| CD21 + B | 6 | 12.8 ± 1.2 | 14.7 ± 1.3 | 13.6 ± 1.4 |
| cells | 12 | 14.6 ± 1.7[a] | 8.7 ± 1.9[b] | 9.3 ± 1.7[b] |

Different subscripts among diets but within a period indicate significant statistical difference, P < .05.

DTH response. Diet did not significantly affect DTH response to Con A or vaccine. Overall, maximal skin induration response to Con A was observed between 24 and 48 hours post injection while maximal response to vaccine was observed at 72 hours.

Other immune functions. Dietary fish oil and flaxseed oil did not significantly influence NK cell cytotoxic activity, IL-2 production by PBMC, or plasma IgG.

EXAMPLE 2

To determine the effects of dietary n-3 PUFA in cats fed lower (14 wt %) total dietary lipids, the n-6:n-3 ratio in all diets was maintained as in Example 1. The experimental design was generally similar to that of Example 1, except that skin hypersensitivity reaction to histamine was also assessed. Results are shown in Table 5.

TABLE 5

Dietary lipid composition: 14 wt % total lipid diet

|  | Control | Fish oil | Flaxseed oil |
|---|---|---|---|
| Lipid (%) | 13.8 | 13.8 | 13.7 |
| Percent of total fatty acids |  |  |  |
| Palmitic acid (16:0) | 23.2 | 22.1 | 22.1 |
| Linoleic acid (18:2n – 6) | 19.5 | 18.4 | 19.8 |
| γ-linolenic acid (18:3n – 6) | 0.2 | 0.2 | 0.2 |
| Arachidonic acid (20:4n – 6) | 0.8 | 0.8 | 0.8 |
| α-Linolenic acid (18:3n – 3) | 0.8 | 0.9 | 4.0 |
| Eicosapentaenoic acid (20:5n – 3) | 0.1 | 2.0 | 0.03 |
| Docosahexaenoic acid (22:6n – 3) | 0.2 | 0.9 | 0.1 |
| Total n – 6 PUFA | 20.9 | 20.0 | 21.1 |
| Total n – 3 PUFA | 1.1 | 4.4 | 4.2 |
| n – 6:n – 3 ratio | 20:1 | 5:1 | 5:1 |
| Vitamin E (mg/kg) | 110 | 110 | 110 |

Blood was collected at weeks 0, 6 and 12 and plasma and peripheral blood mononuclear cells (PBMC) were isolated. The following parameters were assessed:

1. Mitogen-induced PBMC proliferation. Three mitogens, phytohemagglutinin (PHA), concanavalin A (Con A), and pokeweed mitogen (PWM), were used to measure PBMC proliferation in whole blood. [$^3$H]-Thymidine uptake was quantitated by liquid scintillation. Data were expressed as stimulation index.

2. Changes in lymphocyte subpopulations. Blood leukocytes obtained from RBC lysis of whole blood were incubated with monoclonal antibodies against CD5, CD4, CD8, MHCII, and B cell surface markers and an FITC-conjugated secondary antibody. Leukocyte subpopulations were analyzed using flow cytometry.

3. Delayed-type hypersensitivity (DTH) skin response. The DTH response was assessed by measuring skin induration after intradermal (i.d.) challenge with Con A (nonspecific response), vaccine (modified live calcivirus, parvovirus, and Chlamydia psittaci), and saline (control). Skin thickness was measured at 0, 24, 48 and 72 hours after injection with the aid of a pressure-sensitive digital micrometer. The DTH response was expressed as a percent of skin thickness taken at hour 0.

4. Skin hypersensitivity response. Skin inflammatory response was measured in cats in Experiment 2. All cats were injected i.d. with histamine (histamine phosphate) and skin thickness measured at 0, 10, 20, 30, 45 and 60 minute postinjection.

5. Natural killer (NK) cell cytotoxicity. Crandell feline kidney fibroblast cell (CrFK) was used as the target cell to assess NK cell activity in PBMC by the Rose Bangal assay. The effector cell:target cell ratios were 6.25:1, 12.5:1, and 25:1.

6. IL-2 production by PBMC. Whole blood was stimulated with Con A for 48 hours and the supernatant analyzed for IL-2 content using a commercial ELISA kit.

7. Plasma IgG were analyzed by single radial immunodiffusion assay.

8. Fatty acid composition in plasma and skin were analyzed by gas chromatography. Skin biopsies were taken from the flank and immediately frozen in dry ice.

9. Leukotrienes $B_4$ and $B_5$ in skin were analyzed by HPLC/mass spectrometry.

Results

General. Body weights (average 4.8 kg) and food intake (average 76 g/d) was not influenced by diet during the 12-week study period.

Skin Inflammatory Response to Histamine. Cats fed fish oil and flaxseed oil generally showed dramatically reduced skin response to histamine injection during the 60-minute measuring period at week 11 (FIG. 3). Cats fed flaxseed oil had significantly lower response to histamine at 60 minutes postinjection as compared to those fed fish oil. The maximal response to histamine injection in cats fed fish oil and flaxseed oil was approximately 50% that observed in cats fed the control diet (FIG. 4).

Skin Leukotriene Production. Dietary fish oil and flaxseed oil did not alter $LTB_4$ concentration in skin (FIG. 5). However, cats fed fish oil had higher $LTB_5$ production in the skin compared to those fed the control diet. The ratio of $LTB_4$:$LTB_5$ in skin was significantly lower in cats fed fish oil compared to those fed the control or flaxseed oil diet. Results obtained with lower total dietary lipid is similar to that in Example 1.

$LTB_4$ is a proinflammatory response whereas $LTB_5$ is antiinflammatory. Therefore, the lower skin response to histamine in cats fed fish oil can be explained by the lower $LTB_4$:$LTB_5$ ratio in their skin compared to cats fed the control diet. However, even though cats fed the flaxseed oil did not show statistically significant lower skin $LTB_4$:$LTB_5$ ratio than the control diet, they similarly had lower antiinflammatory response to histamine.

Lymphocyte Proliferation. Dietary fish oil and flaxseed oil did not significantly influence PHA- and Con A-stimulated PBMC proliferation. However, cats fed fish oil but not flaxseed oil had significantly lower proliferative response to PWM stimulation compared to those fed the control diet on week 6 (FIG. 6).

Leukocyte Subpopulations. The population of total T cells and $CD4^+$ T cells were significantly lower on week 12 in cats fed fish oil compared to those fed the control and flaxseed oil diets (Table 6). There was no dietary effect on population changes in the T cells, activated macrophages, and B cells at any week.

DTH Response. Dietary fish oil and flaxseed oil did not significantly influence DTH response to Con A or vaccine.

Other Immune Functions. Neither fish oil nor flaxseed oil signficantly affected NK cell cytotoxic activity, IL-2 production by blood PBMC, or plasma IgG concentrations.

TABLE 6

Percentages of blood leukocyte subpopulations in cats fed control, fish oil or flaxseed oil diet for 12 weeks

| | Period, Week | Control | Fish | Flaxseed |
| --- | --- | --- | --- | --- |
| $CD5^+$ T cells | 6 | 44.4 ± 5.1 | 40.3 ± 3.9 | 44.3 ± 5.1 |
| | 12 | 61.3 ± 2.3[a] | 52.6 ± 2.9[b] | 56.9 ± 3.7[a] |
| $CD4^+$ T cells | 6 | 11.2 ± 2.0 | 7.1 ± 1.1 | 12.0 ± 1.5 |
| | 12 | 18.1 ± 1.6[a] | 11.4 ± 1.8[b] | 16.0 ± 2.3[a] |
| $CD8^+$ T cells | 6 | 10.0 ± 2.9 | 10.5 ± 2.8 | 9.0 ± 4.1 |
| | 12 | 18.9 ± 3.1 | 19.5 ± 2.9 | 17.3 ± 4.7 |

TABLE 6-continued

Percentages of blood leukocyte subpopulations in cats fed control, fish oil or flaxseed oil diet for 12 weeks

| | Period, Week | Control | Fish | Flaxseed |
| --- | --- | --- | --- | --- |
| MHC $II^+$ | 6 | 38.9 ± 3.8 | 38.3 ± 3.8 | 42.3 ± 5.1 |
| cells | 12 | 52.0 ± 3.6 | 47.6 ± 2.9 | 51.0 ± 4.1 |
| CD21 + B | 6 | 14.6 ± 1.7 | 16.0 ± 1.2 | 18.0 ± 2.2 |
| cells | 12 | 5.9 ± 1.1 | 7.9 ± 0.9 | 7.4 ± 1.7 |

Different subscripts among diets but within a period indicate significant statistical difference, $P < .05$.

Summary of Results—(Examples 1 and 2)

Dietary n-3 PUFA from fish oil and flaxseed oil decreased the skin inflammatory response to histamine to the same magnitude (assessed in Example 2 only). However, only the fish oil diet significantly increased skin $LTB_5$ concentrations even though the flaxseed oil showed the same tendency. Both fish oil and flaxseed oil generally did not significantly influence a large number of immune parameters. These include lymphocyte proliferation in response to Con A and PHA, certain leukocyte subpopulations, DTH response to vaccine or PHA, NK cell cytotoxicity, IL-2 production, and plasma IgG. However, cats fed fish oil or flaxseed oil in their diets has lower proliferative response to PWM in Example 1 (22% lipid diet), but only cats fed fish oil showed significantly lower PWM-induced response in Example 2 (14% low-lipid diet). In addition, only cats fed fish oil but not flaxseed oil showed lower B cell subpopulations (Example 1) and lower total T and T helper cell subsets (Example 2). This leads to the conclusion that, whereas both fish oil and flaxseed oil can be included in the feline diet to reduce inflammatory response, flaxseed oil offers a better alternative in a lower lipid (14%) diet because flaxseed oil shows minimal immunosuppressive activity compared to fish oil. However, in a high-fat diet, flaxseed oil seems to have greater immunosuppressive action.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A pet food composition comprising an effective inflammatory response-reducing amount, on a dry matter basis, of omega-6 and omega-3 fatty acids in a weight ratio of about 5:1, wherein the omega-3 fatty acids comprises at least about 80% alpha-linoleic acid derived from flaxseed oil, by weight of the omega-3 fatty acids, and wherein the majority of omega-6 fatty acids are derived from flaxseed oil, said composition comprising from about 7 to about 14% by weight total fat, which composition is formulated as a cat food.

2. The pet food composition of claim 1 which at least about 20 wt % of the total fatty acids are omega-6 fatty acids.

3. The pet food composition of claim 1 in which at least about 4 wt % of the total fatly acids are omega-3 fatty acids.

4. The pet food composition of claim 1 in which said omega-3 fatty acids further comprise eicosapentaenoic acid, docosahexaenoic acid, or combinations thereof.

5. The pet food composition of claim 1 which is solid cat food selected from the group consisting of dry kibble, moist chunk foods, moist canned cat food and cat treats.

6. The pet food composition of claim 5 which is fortified with vitamins and micronutrients.

* * * * *